United States Patent [19]
Ding et al.

[11] Patent Number: 5,474,979
[45] Date of Patent: Dec. 12, 1995

[54] NONIRRITATING EMULSIONS FOR SENSITIVE TISSUE

[75] Inventors: Shulin Ding; Walter L. Tien, both of Irvine; Orest Olejnik, Trabuco Canyon, all of Calif.

[73] Assignee: Allergan, Inc., Irvine, Calif.

[21] Appl. No.: 243,279

[22] Filed: May 17, 1994

[51] Int. Cl.$^6$ .......................... A61K 38/13; A61K 47/34
[52] U.S. Cl. .................. 514/11; 514/785; 514/786; 514/912; 514/941; 514/943; 514/975
[58] Field of Search ................. 530/317, 321; 514/9, 11, 785, 786, 912, 913, 914, 915, 941, 943, 975, 178, 179, 180, 181, 420, 784; A61K 9/107, 47/14

[56] References Cited

U.S. PATENT DOCUMENTS

| | | | |
|---|---|---|---|
| 4,347,238 | 8/1982 | Hollingsbee | 514/179 |
| 4,839,342 | 6/1989 | Kaswan | 514/11 |
| 4,990,337 | 2/1991 | Kurihara et al. | 424/427 |
| 4,996,193 | 2/1991 | Hewitt et al. | 514/11 |
| 5,051,402 | 9/1991 | Kurihara et al. | 514/11 |
| 5,364,632 | 11/1994 | Benita et al. | 514/943 |

*Primary Examiner*—Jeffrey E. Russel
*Attorney, Agent, or Firm*—Walter A. Hackler

[57] ABSTRACT

A pharmaceutical composition is disclosed in the form of a nonirritating emulsion which includes at least one cyclosporin in admixture with a higher fatty acid glyceride and polysorbate 80. More particularly, the cyclosporin may be cyclosporin A and the higher fatty acid glyceride may be castor oil. Composition has been found to be of a high comfort level and low irritation potential suitable for delivery of medications to sensitive areas such as ocular tissues. In addition, the composition has stability for up to nine months without crystallization of cyclosporin.

8 Claims, No Drawings

NONIRRITATING EMULSIONS FOR SENSITIVE TISSUE

The present invention generally relates to novel pharmaceutical compositions incorporating chemicals which are poorly soluble in water and is more particularly related to a novel ophthalmic emulsion including cyclosporin in admixture with castor oil and polysorbate 80 with high comfort level and low irritation potential.

Cyclosporins are a group of nonpolar cyclic oligopeptides with known immunosuppressant activity. In addition, as set forth in U.S. Pat. No. 4,839,342, cyclosporin (sometimes referred to in the literature as "cyclosporine") has been found as effective in treating immune medicated keratoconjunctivitis sicca (KCS or dry eye disease) in a patient suffering therefrom.

As hereinabove noted, cyclosporin comprises a group of cyclic oligopeptides and the major component thereof is cyclosporin A ($C_{62}H_{111}N_{11}O_{12}$) which has been identified along with several other minor metabolites, cyclosporin B through I. In addition, a number of synthetic analogs have been prepared.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

It should be appreciated that reference to the term "cyclosporin" or "cyclosporins" is used throughout the present specification in order to designate the cyclosporin component in the composition of the present invention.

However, this specific reference is intended to include any individual member of the cyclosporin group as well as admixtures of two or more individual cyclosporins, whether natural or synthetic.

The activity of cyclosporins, as hereinabove noted, is as an immunosuppressant and in the enhancement or restoring of lacrimal gland tearing.

Unfortunately, the solubility of cyclosporin in water is extremely low and as elaborated in U.S. Pat. No. 5,051,402, it has been considered not merely difficult but practically impossible to prepare a pharmaceutical composition containing cyclosporin dissolved in an aqueous medium.

As reported, the solubility of cyclosporin in water is between about 20 μg/ml to 30 μg/ml for cyclosporin A. Hence, heretofore prepared formulations incorporating cyclosporin have been prepared as oily solutions containing ethanol. However, these preparations limit the bioavailability to oral preparations and this is believed to be due to the separation of cyclosporin as a solid immediately after it comes into contact with water, such as in the mouth or eye of a patient.

In the case of injectable preparations of cyclosporin, they first must be diluted with physiological saline before intravenous administration but this is likely to result in the precipitation of cyclosporin and therefore may be considered undesirable for intravenous administration.

Surface active agents such as polyoxyethylated castor oil have been utilized as solubilizers to inject preparations in order to prevent cyclosporin from separating. However, this also may give rise to safety problems (see U.S. Pat. No. 5,051,402).

The practical usefulness of cyclosporin would be greatly enhanced if administration thereof could be effective; for example, cyclosporin's effectiveness in the treatment of ocular symptoms of Behcet's Syndrome. However, if it is administered orally for the treatment of these symptoms, the accompanying side effects due to systemic circulation may cause adverse reactions such as hypertrichosis or renal dysfunction.

On the other hand, if oily preparations containing cyclosporin are applied directly to the eyes, irritation or a clouding of visual field may result. This plus the difficulty in formulating cyclosporin limits its use in formulations that would be useful during keratoplasty as well in the treatment of herpetic keratitis and spring catarrh.

Heretofore, as for example in U.S. Pat. No. 5,051,402, attempts have been made to dissolve sufficient cyclosporin in an aqueous solvent system so as to reach an effective concentration for treatment. Importantly, this solvent system does not contain any surface active agent such as polyoxyethylated castor oil.

Conceptually, the purpose of dissolving the cyclosporin in an aqueous solvent system is to enable contact with body fluids which would merely constitute dilution of the aqueous solvent system which hopefully would eliminate the immediate precipitation of cyclosporin when contacted with the water content of the body fluids.

For direct use in the eye, cyclosporin has been formulated with a number of pharmaceutically acceptable excipients, for example, animal oil, vegetable oil, an appropriate organic or aqueous solvent, an artificial tear solution, a natural or synthetic polymer or an appropriate membrane.

Specific examples of these pharmaceutically acceptable excipients, which may be used solely or in combination, are olive oil, arachis oil, castor oil, mineral oil, petroleum jelly, dimethyl sulfoxide, chremophor, liposomes, or liposome-like products or a silicone fluid, among others.

In summary, a great deal of effort has been expended in order to prepare a pharmaceutical composition containing cyclosporin dissolved in an aqueous medium or cyclosporin prepared as an oily solution. However, successful formulations have yet to be accomplished as evidenced by the lack of commercial products.

As hereinabove noted, it has been reported that cyclosporin has demonstrated some solubility in oily preparations containing higher fatty acid glycerides such as olive oil, peanut oil, and/or castor oil. These formulations frequently produce an unpleasant sensation when applied to the eye because of stimulation or the viscousness which is characteristic of these oils.

Another drawback of these formulations is that they contain a high concentration of oils, and oils exacerbate the symptoms of certain ocular surface diseases such as dry eyes, indicated by cyclosporin. Therefore, these oily formulations may not be clinically acceptable. Additionally, these formulations often suffer from physical instability due to cyclosporin's propensity to undergo conformational change and crystallize out. The crystallization problem has been noticed in formulations containing corn oil or medium chain triglycerides. Lastly, these formulations often have a low thermodynamic activity (degree of saturation) of cyclosporin which leads to a poorer drug bioavailability.

It may be possible to minimize the problems related to unpleasant sensation and syndrome exacerbation by reducing the oil content and dispersing the oil phase in water into an emulsion. However, it is not an easy task to formulate an ophthalmic emulsion because one indispensable class of ingredients in an emulsion system is emulsifiers, and the majority of emulsifiers is highly irritating to the eyes.

The present invention is directed to an emulsion system which utilizes higher fatty acid glycerides but in combination with polysorbate 80 which results in an emulsion with a high comfort level and low irritation potential suitable for delivery of medications to sensitive areas such as ocular tissues.

SUMMARY OF THE INVENTION

In accordance with the present invention, a nonirritating pharmaceutical composition with high comfort level and low irritation potential suitable for delivery to sensitive areas such as ocular tissues comprises cyclosporin in admixture with an emulsifying amount of a higher fatty acid glycerol and polysorbate 80. More particularly, the composition may comprise cyclosporin A and the higher fatty acid glyceride may comprise castor oil.

Preferably, the weight ratio of the castor oil to the polysorbate 80 is between about 0.3 to about 30 and a weight ratio of the cyclosporin to castor oil is below 0.16. More preferably, the weight ratio of castor oil to polysorbate 80 is between 0.5 and 12.5, and the weight ratio of cyclosporin to castor oil is between 0.12 and 0.02.

When cyclosporin is dissolved in the oil phase in accordance with the present invention, the emulsion is found to be physically stable upon long term storage. No crystallization of cyclosporin was noticed after nine months at room temperature. Moreover, the cyclosporin emulsion is formulated in such a way that the drug has reasonably high thermodynamic activity, yet without the crystallization problem.

DETAILED DESCRIPTION

As hereinabove noted, cyclosporin is available as a mixture in which the principal ingredient is cyclosporin A with significant, but smaller, quantities of other cyclosporins such as cyclosporin B through I. However, as also hereinabove noted, the present invention may be applied to either a pure cyclosporin or to a mixture of individual cyclosporins.

The discovery on which the present invention is founded relates to a combination of a higher fatty acid glyceride and an emulsifier and dispersing agent, polysorbate 80. The selection of these components could not have been anticipated on the basis of conventional thinking.

For example, although it is well-known that cyclosporin may be used in combination with castor oil, this combination is irritating to sensitive tissues such as the eye. Thus, conventional teaching in the art is away from a formulation which utilizes a higher fatty acid glyceride, such as castor oil, and cyclosporin.

Stated another way, there is no way of deducing that the use of an emulsifier and dispersing agent such as polysorbate 80 will reduce the irritation potential of an emulsion utilizing castor oil. There are no examples of polysorbate in combination with castor oil which, when admixed to cyclosporin, produces an emulsion with a high comfort level and low irritation potential suitable for the delivery of medication to sensitive areas such as ocular tissues.

The present invention achieves a stable solution state of cyclosporin. This stable solution state is another important performance characteristic differentiating the present invention from the conventional oil systems. Cyclosporin is notorious for its tendency to precipitate out in conventional oil systems in which it is fully dissolved initially.

In accordance with the present invention, the emulsions can be further stabilized using a polyelectrolyte, or polyelectrolytes if more than one, from the family of cross-linked polyacrylates, such as carbomers and Pemulen®.

Pemulen® is a registered trademark of B. F. Goodrich for polymeric emulsifiers and commercially available from B. F. Goodrich Company, Specialty Polymers & Chemicals Division, Cleveland, Ohio. Pemulens are Acrylates/C10-30 Alkyl Acrylate Cross-Polymers. They are high molecular weight co-polymers of acrylic acid and a long chain alkyl methacrylate cross-linked with allyl ethers of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

While the preferable medications in accordance with the present invention include cyclosporin, other chemicals which are poorly soluble in water such as indomethacin and steroids such as androgens, prednisolone, prednisolone acetate, fluorometholone, and dexamethasones, may be emulsified with castor oil and polysorbate 80 resulting in a composition with similar low irritation potential.

The invention is further illustrated by the following examples with all parts and percentages expressed by weight. The cyclosporin used in the examples was supplied by Sandoz.

| Example 1 | | | | | |
|---|---|---|---|---|---|
| | A | B | C | D | E |
| Cyclosporin A | 0.40% | 0.20% | 0.20% | 0.10% | 0.05% |
| Castor oil | 5.00% | 5.00% | 2.50% | 1.25% | 0.625% |
| Polysorbate 80 | 1.00% | 1.00% | 1.00% | 1.00% | 1.00% |
| Pemulen ® | 0.05% | 0.05% | 0.05% | 0.05% | 0.05% |
| Glycerine | 2.20% | 2.20% | 2.20% | 2.20% | 2.20% |
| NaOH | qs | qs | qs | qs | qs |
| Purified water | qs | qs | qs | qs | qs |
| pH | 7.2–7.6 | 7.2–7.6 | 7.2–7.6 | 7.2–7.6 | 7.2–7.6 |

| Example 2 | | | | |
|---|---|---|---|---|
| | A | B | C | D |
| Castor oil | 5.00% | 2.50% | 1.25% | 0.625% |
| Polysorbate 80 | 1.00% | 1.00% | 1.00% | 1.00% |
| Pemulen ® | 0.05% | 0.05% | 0.05% | 0.05% |
| Glycerine | 2.20% | 2.20% | 2.20% | 2.20% |
| NaOH | qs | qs | qs | qs |
| Purified water | qs | qs | qs | qs |
| pH | 7.2–7.6 | 7.2–7.6 | 7.2–7.6 | 7.2–7.6 |

| Example 3 | |
|---|---|
| | A |
| Castor oil | 2.50% |
| Polysorbate 80 | 0.75% |
| Carbomer 1382 | 0.05% |
| Glycerine | 2.20% |
| NaOH | qs |
| Purified water | qs |
| pH | 7.2–7.6 |

| Example 4 | |
|---|---|
| | A |
| Castor oil | 5.00% |

-continued

| | |
|---|---|
| Polysorbate 80 | 0.75% |
| Carbomer 981 | 0.05% |
| Glycerin | 2.20% |
| NaOH | qs |
| Purified water | qs |
| pH | 7.2–7.6 |

The formulations set forth in Examples 1–4 were made for treatment of keratoconjunctivitis sicca (dry eye) syndrome with Examples 2, 3 and 4 without the active ingredient cyclosporin utilized to determine the toxicity of the emulsified components.

The formulations in Examples 1–4 were applied to rabbit eyes eight times a day for seven days and were found to cause only slight to mild discomfort and slight hyperemia in the rabbit eyes. Slit lamp examination revealed no changes in the surface tissue. In addition, the cyclosporin containing castor oil emulsion, as hereinabove set forth in Examples 1A–1D, was also tested for ocular bioavailability in rabbits; and the therapeutic level of cyclosporin was found in the tissues of interest after dosage. This substantiates that cyclosporin in an ophthalmic delivery system is useful for treating dry eye as set forth in U.S. Pat. No. 4,839,342.

In addition, no difference in toxicity was found between formulations with cyclosporin (Examples 1A–1D) and formulations without cyclosporin (Examples 2–4).

The formulations set forth in Examples 1–4 were found to be physically stable upon long term storage. With regard to formulations 1A–1D, no crystallization of cyclosporin was noticed after nine months at room temperature.

Further, other higher fatty acid glycerides such as olive oil, peanut oil and the like may also be utilized with the polysorbate 80 with similar results regarding biotoxicity.

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A pharmaceutical composition comprising a nonirritating emulsion of at least one cyclosporin in admixture with a higher fatty acid glyceride, polysorbate 80 and an emulsion stabilizing amount of Pemulen in water suitable for topical application to ocular tissue.

2. The pharmaceutical composition according to claim 1 wherein the cyclosporin comprises cyclosporin A.

3. The pharmaceutical composition according to claim 2 wherein the weight ratio of the higher fatty acid glyceride to the polysorbate 80 is between about 0.3 and about 30.

4. The pharmaceutical composition according to claim 3 wherein the higher fatty acid glyceride comprises castor oil and the weight ratio of cyclosporin to castor oil is below about 0.16.

5. The composition according to claim 1 wherein the higher fatty acid glyceride and polysorbate 80 are present in amounts sufficient to prevent crystallization of cyclosporin for a period of up to about nine months.

6. A pharmaceutical emulsion comprising of cyclosporin A, castor oil, Pemulen, glycerine, polysorbate 80 water in amounts sufficient to prevent crystallization of cyclosporin A for a period of up to about nine months, said pharmaceutical emulsion being suitable for topical application to ocular tissue.

7. The pharmaceutical emulsion according to claim 6 wherein the cyclosporin A is present in an amount of between about 0.05 to and about 0.40%, by weight, the castor oil is present in an amount of between about 0.625%, by weight, and about 5.0%, by weight, the polysorbate 80 is present in an amount of about 1.0%, by weight, the Pemulen is present in an amount of about 0.05%, by weight, and the glycerine is present in an amount of about 2.2%, by weight.

8. A pharmaceutical emulsion consisting of between about 0.05% and about 0.40%, by weight, cyclosporin A, between about 0.625% and about 5.0%, by weight, castor oil, about 1.0%, by weight, polysorbate 80, about 0.05%, by weight, Pemulen and about 2.2%, by weight, glycerine in water with a pH of between about 7.2 and 7.6 suitable for topical application to ocular tissue.

* * * * *

(12) EX PARTE REEXAMINATION CERTIFICATE (9030th)
United States Patent
Ding et al.

(10) Number: US 5,474,979 C1
(45) Certificate Issued: May 29, 2012

(54) NONIRRITATING EMULSIONS FOR SENSITIVE TISSUE

(75) Inventors: Shulin Ding, Irvine, CA (US); Walter L. Tien, Irvine, CA (US); Orest Olejnik, Trabuco Canyon, CA (US)

(73) Assignee: Allergan, Inc., Irvine, CA (US)

Reexamination Request:
No. 90/009,944, Aug. 27, 2011

Reexamination Certificate for:
Patent No.: 5,474,979
Issued: Dec. 12, 1995
Appl. No.: 08/243,279
Filed: May 17, 1994

(51) Int. Cl.
*A61K 9/00* (2006.01)
*A61K 9/107* (2006.01)
*A61K 38/00* (2006.01)
*A61K 38/12* (2006.01)
*A61K 38/13* (2006.01)
*A61K 47/10* (2006.01)
*A61K 47/14* (2006.01)
*A61K 47/32* (2006.01)
*A61K 47/34* (2006.01)
*A61P 27/02* (2006.01)

(52) U.S. Cl. ............ 514/20.5; 514/20.8; 514/785; 514/786; 514/912; 514/941; 514/943; 514/975

(58) Field of Classification Search ............... None
See application file for complete search history.

(56) References Cited

To view the complete listing of prior art documents cited during the proceeding for Reexamination Control Number 90/009,944, please refer to the USPTO's public Patent Application Information Retrieval (PAIR) system under the Display References tab.

*Primary Examiner* — Gary Kunz

(57) ABSTRACT

A pharmaceutical composition is disclosed in the form of a nonirritating emulsion which includes at least one cyclosporin in admixture with a higher fatty acid glyceride and polysorbate 80. More particularly, the cyclosporin may be cyclosporin A and the higher fatty acid glyceride may be castor oil. Composition has been found to be of a high comfort level and low irritation potential suitable for delivery of medications to sensitive areas such as ocular tissues. In addition, the composition has stability for up to nine months without crystallization of cyclosporin.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *